United States Patent
Henderson et al.

(10) Patent No.: US 6,716,167 B1
(45) Date of Patent: Apr. 6, 2004

(54) MEDICAL DIAGNOSTIC ULTRASOUND IMAGING SYSTEM WITH A PATIENT SUPPORT SURFACE

(75) Inventors: Richard W. Henderson, Fremont, CA (US); David E. Burris, Santa Cruz, CA (US); Jeff N. Gamelsky, Palo Alto, CA (US)

(73) Assignee: Siemens Medical Soluions USA, Inc., Malvern, PA (US)

( * ) Notice: Subject to any disclaimer, the term of this patent is extended or adjusted under 35 U.S.C. 154(b) by 0 days.

(21) Appl. No.: 09/964,278

(22) Filed: Sep. 25, 2001

(51) Int. Cl.[7] .................................................. A61B 8/00
(52) U.S. Cl. ...................................................... 600/437
(58) Field of Search ................................. 600/407–471; 5/6, 600–624, 83.1, 85.1, 86.1, 630, 631–650; 280/29, 651, 652, 657, 656, 659; 297/4, 29; 378/62–65, 101, 102, 167, 177, 188, 189, 193, 204, 210; 606/20, 22; 604/890.1, 891.1; 73/625; 367/7, 11; 601/2, 3

(56) References Cited

U.S. PATENT DOCUMENTS

| | | |
|---|---|---|
| 5,117,521 A | 6/1992 | Foster et al. |
| 5,335,651 A | 8/1994 | Foster et al. |
| 5,337,845 A | 8/1994 | Foster et al. |
| 5,353,354 A * | 10/1994 | Keller et al. ................. 382/128 |
| 5,370,111 A | 12/1994 | Reeder et al. |
| 5,415,169 A * | 5/1995 | Siczek et al. ................. 600/427 |
| 5,457,831 A | 10/1995 | Foster et al. |
| 5,609,152 A * | 3/1997 | Pellegrino et al. ........... 600/429 |
| 5,703,922 A * | 12/1997 | Rattner ........................ 378/65 |
| 5,924,988 A | 7/1999 | Burris et al. |
| 6,073,942 A * | 6/2000 | Heneveld, Sr. ......... 280/33.991 |

* cited by examiner

Primary Examiner—Ali M. Imam

(57) ABSTRACT

The preferred embodiments described herein provide a medical diagnostic ultrasound imaging system with a patient support surface. In one preferred embodiment, a medical diagnostic ultrasound imaging system is provided that is integrated with a base coupled with a patient support surface. In another preferred embodiment, a medical diagnostic ultrasound imaging system is carried by a medical diagnostic ultrasound imaging system cart that is detachably coupled with a base coupled with a patient support surface. In yet another preferred embodiment, a first medical diagnostic ultrasound imaging system assembly is provided that is integrated with a base coupled with a patient support surface. A medical diagnostic ultrasound imaging system cart is also provided that carries a second medical diagnostic ultrasound imaging system assembly and is detachably and electrically coupled with the base. Other preferred embodiments are provided, and each of these preferred embodiments can be used alone or in combination with one another.

22 Claims, 4 Drawing Sheets

MEDICAL DIAGNOSTIC ULTRASOUND IMAGING SYSTEM WITH A PATIENT SUPPORT SURFACE

BACKGROUND

During an ultrasound examination, a patient rests on a support surface, such as a gurney or bed, and a medical diagnostic ultrasound imaging system is positioned adjacent the patient support surface. A sonographer sitting or standing near the ultrasound system uses one hand to hold an ultrasonic transducer probe in contact with the patient and uses his other hand to interact with the ultrasound system's user interface (e.g., its control panel) while looking at the ultrasound system's display device. This set-up requires the sonographer to position his body between the patient support surface and the ultrasound system, which sometimes interrupts the sonographer's natural position for scanning the patient. Sonographers can find this body position uncomfortable and inefficient.

There is a need, therefore, for a medical diagnostic ultrasound imaging system that overcomes the disadvantages described above.

SUMMARY

The present invention is defined by the following claims, and nothing in this section should be taken as a limitation on those claims.

By way of introduction, the preferred embodiments described below provide a medical diagnostic ultrasound imaging system with a patient support surface. In one preferred embodiment, a medical diagnostic ultrasound imaging system is provided that is integrated with a base coupled with a patient support surface. In another preferred embodiment, a medical diagnostic ultrasound imaging system is carried by a medical diagnostic ultrasound imaging system cart that is detachably coupled with a base coupled with a patient support surface. In yet another preferred embodiment, a first medical diagnostic ultrasound imaging system assembly is provided that is integrated with a base coupled with a patient support surface. A medical diagnostic ultrasound imaging system cart is also provided that carries a second medical diagnostic ultrasound imaging system assembly and is detachably and electrically coupled with the base. Other preferred embodiments are provided, and each of these preferred embodiments can be used alone or in combination with one another.

The preferred embodiments will now be described with reference to the attached drawings.

DETAILED DESCRIPTION OF THE PRESENTLY PREFERRED EMBODIMENTS

By way of overview, the preferred embodiments described herein provide a medical diagnostic ultrasound imaging system with a patient support surface. These preferred embodiments can improve the ergonomic envelope for a sonographer and the usability of an ultrasound system within the ultrasound scanning environment by accommodating the sonographer's natural position for scanning with system control panel operation and display viewing. This results in a more natural body position for the sonographer, making the sonographer's job easier, more efficient, more comfortable, and less-likely to cause injury. By way of example, a bed can have an ultrasound system permanently built into its understructure such that the bed is the ultrasound system. As another example, a bed can be designed to receive a mobile ultrasound system such that when the two components are coupled together, they ergonomically position the control panel and display with respect to the patient support surface. The ultrasound system can later be separated from the bed and transported to a different location for a portable examination.

Figure 1:
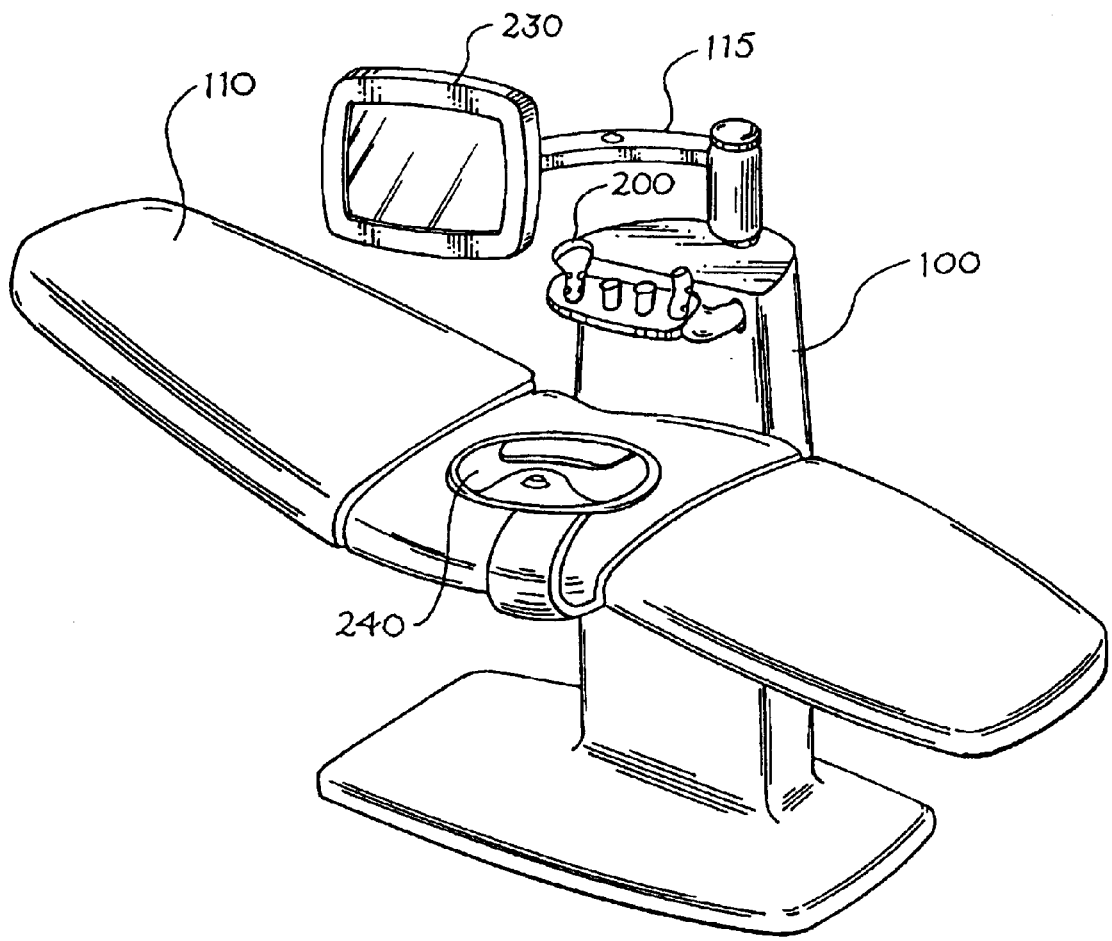
FIG. 1 is an illustration of a medical diagnostic ultrasound imaging system with a patient support surface of a preferred embodiment.

Turning now to the drawings, FIG. 1 is an illustration of a medical diagnostic ultrasound imaging system with a patient support surface of a preferred embodiment. As shown in FIG. 1 a base 100 is coupled with a patient support surface 110. As used herein, the term "coupled with" means directly coupled with or indirectly coupled with through one or more named or unnamed intervening components. As also used herein, the term "patient support surface" refers to any suitable surface that supports a patient undergoing an ultrasound examination with the ultrasound system. A patient support surface can be, for example, a gurney, bed, examination table, cot, or chair for the patient to sit, lie, or stand on. Here, the patient support surface 110 takes a form similar to a "dentists chair."

Figure 2:
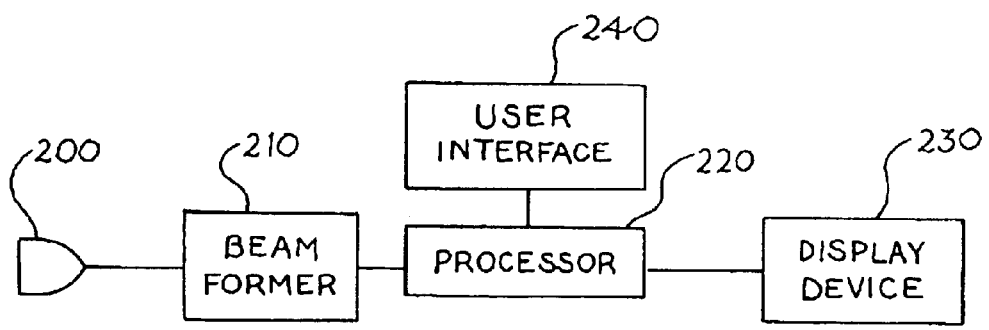
FIG. 2 is a block diagram of components of a medical diagnostic ultrasound imaging system of a preferred embodiment.

In this preferred embodiment, the base 100 is a stationary, free-standing unit that supports the patient support surface 100 at its center location, and the medical diagnostic ultrasound imaging system is integrated with the base 100. The ultrasound system is "integrated" in the sense that the primary use of the ultrasound system is with the base 100, and the ultrasound system is not detachably coupled with the base 100 for modular use in a different base unit. As shown in the block diagram of FIG. 2, the medical diagnostic ultrasound imaging system comprises a transducer probe 200, a beamformer 210 coupled with the transducer probe 200, a processor 220 coupled with the beamformer 210, a display device 230 coupled with the processor 220, and a user interface 240 (e.g., a control panel) coupled with the processor 220. Here, the transducer probe 200, display device 230, and user interface 240 are located on the external portion of the base 100, while the beamformer 210 and the processor 220 are internally located in the base 100. It should be noted that although the ultrasound system in "integrated" with the base, the transducer probe 200 can be removable such that different transducer probes can be coupled and used with the ultrasound system. In this embodiment, the user interface 240 is moveable with respect to the patient support surface 110 via a swiveling arm. The user interface 240 can also swing downward to provide patient access for getting on or off the patient support surface 110. The display device 230 (here, a flat panel display device) is movable with respect to the patient support surface 110 via swiveling arms 115 that connect the display device 230 to the base 110.

For simplicity, the term "processor" is used to broadly refer to the appropriate hardware and/or software components of the ultrasound system that can be used to implement the functionality described herein. It should be understood that any appropriate hardware (analog or digital) or software can be used and that the embodiments described herein can be implemented exclusively with hardware. Further, the processor 220 can be separate from or combined with (in part or in whole) other processors of the ultrasound system (including attendant processors), which are not shown in FIG. 2 or described herein for simplicity. Further, it should be noted that the ultrasound imaging system can comprise additional components. Additionally, the ultrasound system can be used with any suitable imaging mode (e.g., B-mode imaging, Doppler imaging, tissue harmonic imaging, contrast agent harmonic imaging, etc.), and the transducer probe 200 can have a transducer of any suitable type (e.g., 1D, 1.5D, plano-concave, single element, phased-array, etc.).

In operation, a patient rests on the support surface 110 while a sonographer sitting or standing adjacent the patient faces both the patient and the ultrasound system's user interface 240 and display device 230. The sonographer contacts the transducer probe 200 with the patient, and the ultrasound system's processor 220 causes the beamformer 210 to apply a voltage to the transducer 200 to cause it to vibrate and emit an ultrasonic beam into the portion of the patient's body in contact with the transducer 200. Ultrasonic energy reflected from the patient's body impinges on the transducer 200, and the resulting voltages created by the transducer 200 are received by the beamformer 210. The processor 220 processes the sensed voltages to create an ultrasound image associated with the reflected signals and displays the image on the display device 230. The user interface 240 can be used, for example, to adjust parameters used in the transmit, receive, and display operations.

Figure 3:
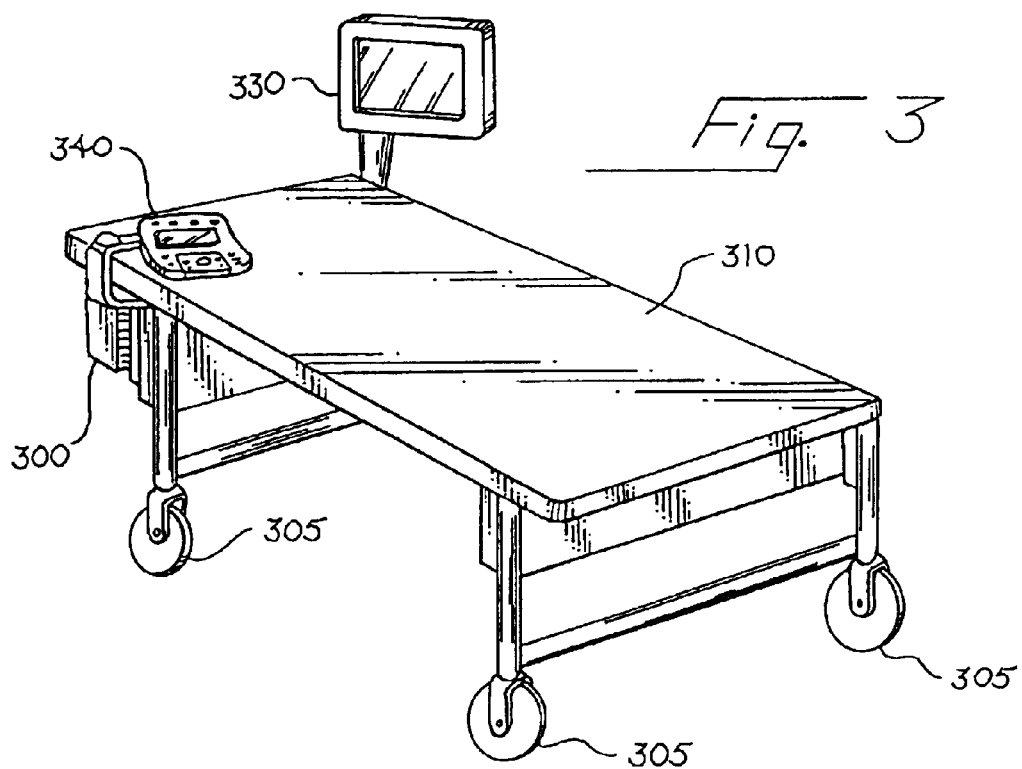
FIG. 3 is an illustration of a medical diagnostic ultrasound imaging system with a patient support surface of another preferred embodiment.

In the preferred embodiment shown in FIG. 1, the base 100 was stationary, and a patient is brought to the base 100 for examination. Alternatively, the base 100 can be mobile, allowing the ultrasound imaging system and patient support surface to be brought to the patient. For example, in the preferred embodiment shown in FIG. 3, the base 300 takes the form of a gurney with a plurality of wheeled legs 305, and the patient support surface 310 is a bed. As with the embodiment shown in FIG. 1, the ultrasound system in integrated in the base 300, and the user interface 340 and the display device 330 are externally located, while the beamformer and processor are internally located. Similar to the embodiment shown in FIG. 1, both the user interface 340 and the display device 330 are movable with respect to the patient support surface 310. As noted above, because the base 300 is movable, the ultrasound system and patient support surface 310 can be wheeled to a patient. Additionally, with the patient resting on the patient support surface 310, the patient and the ultrasound system can be wheeled together as a single unit.

Figure 4:
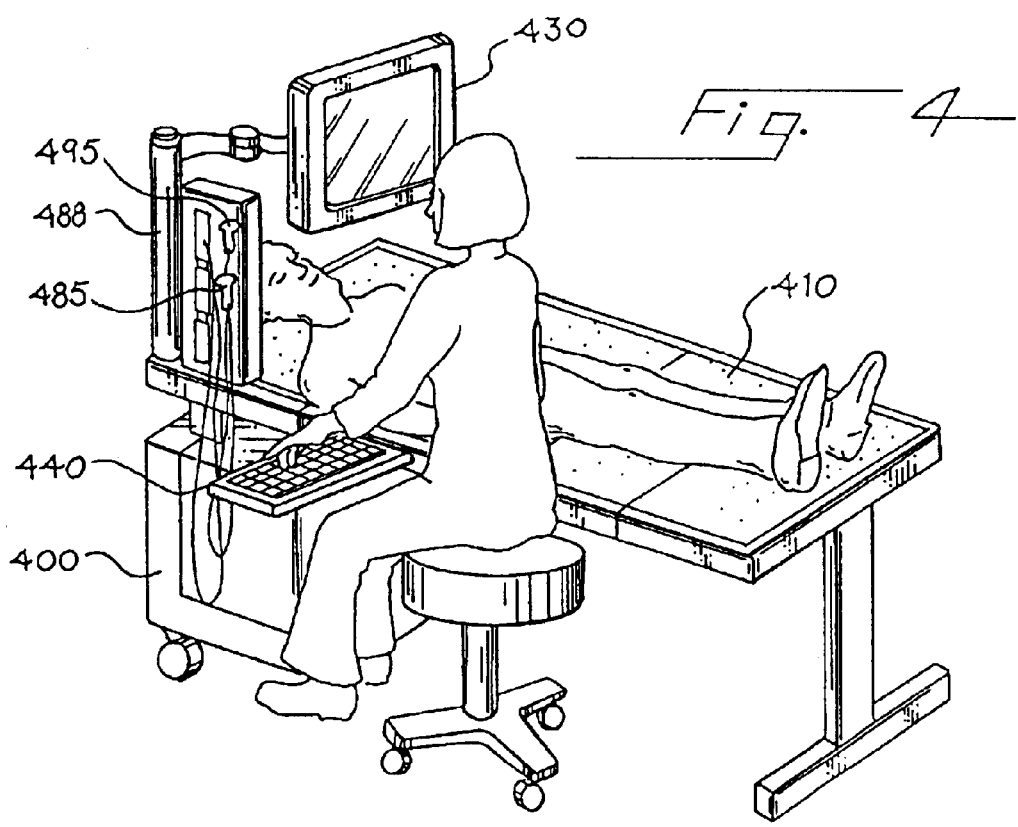
FIG. 4 is an illustration of a medical diagnostic ultrasound imaging system with a patient support surface of another preferred embodiment.
Figure 5A:
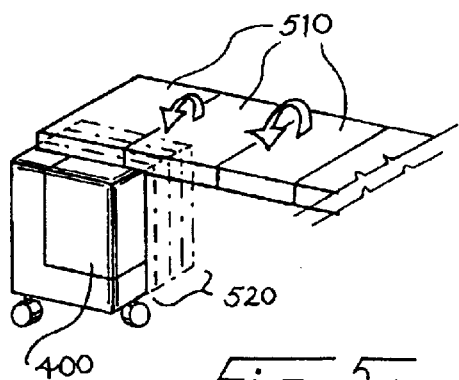
FIGS. 5A, 5B, and 5C illustrate folding of the patient support surface of FIG. 4.
Figure 5B:
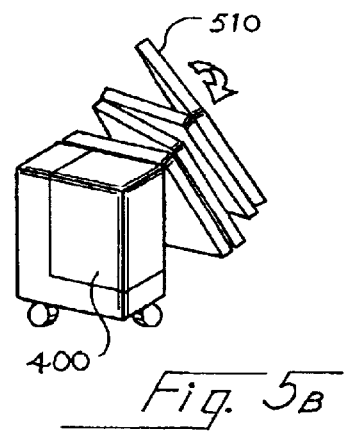
Figure 5C:
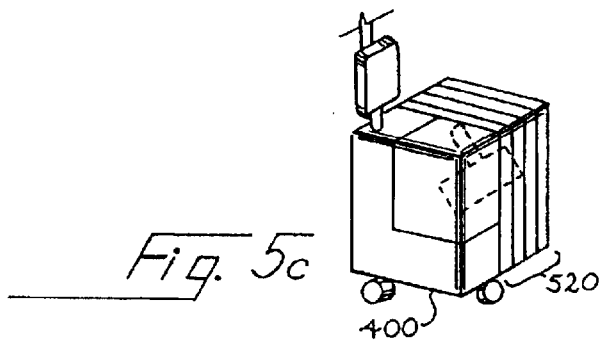

To make an integrated ultrasound system/patient support surface easier to move, the patient support surface 410 can be foldable, as shown in the preferred embodiment of FIG. 4. In the embodiment of FIG. 4, the ultrasound imaging system is integrated in the base 400, and an "IV-like" pole 480 upwardly extends from the base 400 and supports an articulating flat screen display device 430. An assembly 485 attaches to the pole 480 and supports several transducer probes 495. The display device 430 pivots about the pole 480, and the user interface 440 is also adjustable and movable with respect to the patient support surface 410. In this preferred embodiment, the patient support surface 410 comprises a lightweight frame and fabric divided into a plurality of foldable segments 510 (see FIG. 5A). As illustrated in FIGS. 5A and 5B, to make the overall unit easier to transport, the foldable segments 510 can be folded in a scissors-like manner into a compacted unit (shown in phantom as 520 in FIG. 5A). Here, each foldable segment 510 has the same width as the base 400, and one of the foldable segments 510 is coupled with the base 400 via a hinge. In this way, the compacted unit 520 of foldable segments 510 fits in the same lateral "footprint" as the base 400, making the ultrasound system easy to transport (see FIG. 5C). When the ultrasound system is brought to its destination, the patient support surface 410 folds out of the ultrasound system.

Figure 6:
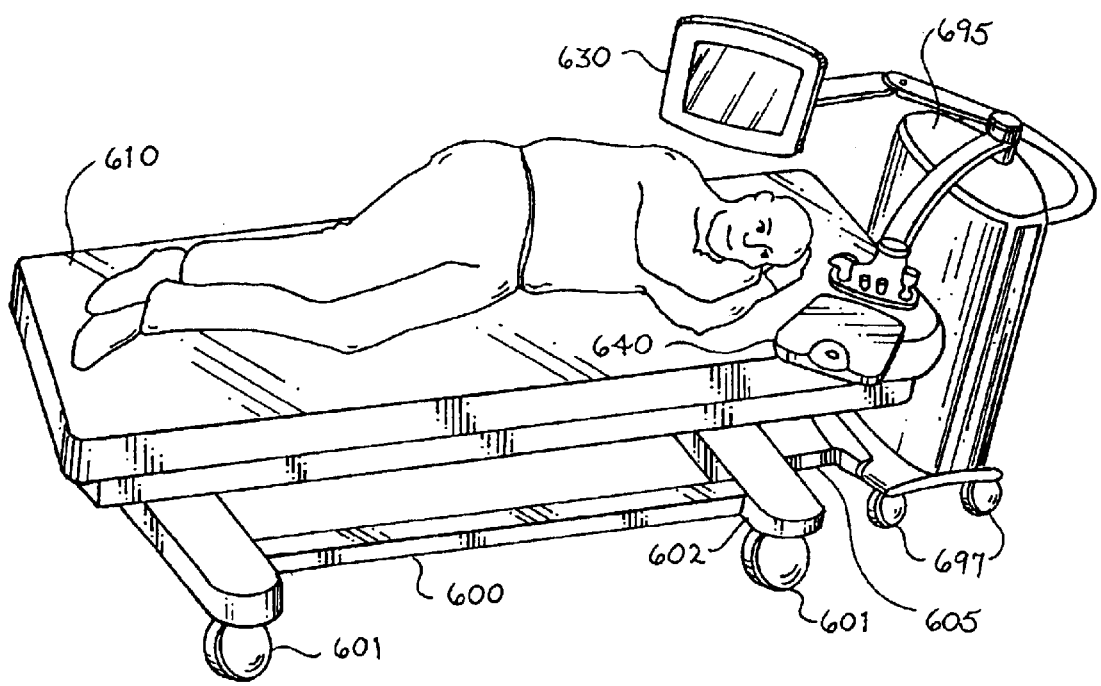
FIG. 6 is an illustration of a medical diagnostic ultrasound imaging system with a patient support surface of another preferred embodiment.

In the preferred embodiments described above, an ultrasound imaging system was integrated with a base coupled with a patient support surface. In an alternate embodiment, the ultrasound imaging system is detachably coupled with the base, allowing the ultrasound system to be separated from the patient support surface in order to go mobile for portable examinations. For example, in the embodiment shown in FIG. 4, some of the electronic components of the ultrasound system (e.g., the processor and the beamformer) can be located in a small, detachable box in the base 400 that can be transported to and used with a different base unit. Another example of this is shown in FIG. 6. In the embodiment shown in FIG. 6, a mobile medical diagnostic ultrasound imaging system cart 695 with wheels 697 carries the ultrasound system. A base 600 coupled with a patient support surface 610 also has wheels 601 and is movable separate from the cart 695. The base 600 and the cart 695, however, can be mechanically coupled together to provide a combined ultrasound system and patient support surface. Any suitable mechanism can be used to physically couple the base 600 and the cart 695. For example, in FIG. 6, the base 600 comprises a lobster-claw-like clamping mechanism 605 that clamps onto a surface of the cart 695. In an alternate embodiment, the clamping mechanism is located on the cart 695 and can clamp onto a rail 602 that runs along the bottom of the base 600. In this way, the cart 695 can be positioned anywhere along the base 600 (e.g., at the front, rear, or sides of the bed). After an ultrasound examination, the base 600 and the cart 695 can be decoupled, and either or both can be moved to a separate location. For example, after being detached, the cart 695 can be moved to a different examination room and attached to a different base. Alternatively, the cart 695 can stay in the same examination room, and the patient can be wheeled on the patient support surface 610 to a different room.

In this preferred embodiment, both the display device 630 and the user interface 640 are movable with respect to the patent support surface 610 so that the sonographer can position these elements to a desired ergonomic position. Here, the base 600 and patient support surface 610 provide the necessary mechanical stability to allow the display device 630 and/or user interface 640 to extend the full distance away from the cart 695. That is, the cart 695 would be mechanically unstable (e.g, the cart 695 would tip over) if the display device 630 and/or user interface 640 were allowed to extend the full distance away from the cart 695 when the cart 695 is not coupled with the base 600. To prevent this from happening, it is preferred that the cart 695 comprise a mechanism that prevents the display device 630 and/or user interface 640 from over-extending (or extending at all) when the cart 695 is not coupled with the base 600. For example, the clamp mechanism 605 can contain a key that fits into a receiving member on the cart 695. When the cart 695 is detached from the base 600, the key is not engaged in the receiving member, and the movement of the display device 630 and/or user interface 640 is limited (like a car's steering wheel when a car key is not inserted into the steering column). When the cart 695 is coupled with the base 600, the key engages the receiving member, and the display device 630 and/or user interface 640 can be freely moved.

Figure 7:
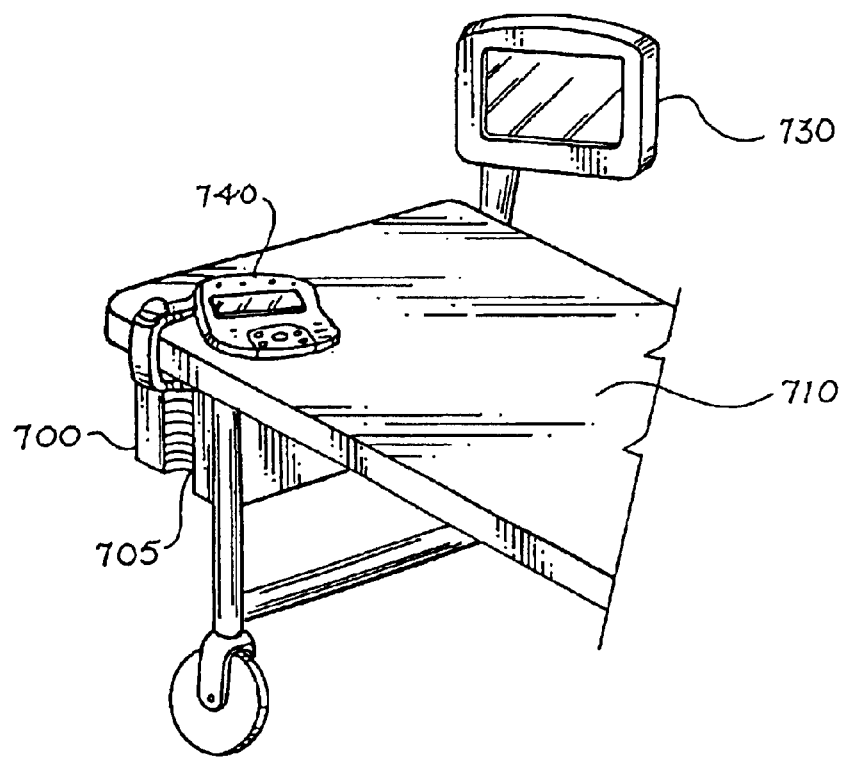
FIG. 7 is an illustration of a medical diagnostic ultrasound imaging system with a patient support surface of another preferred embodiment.

In the preferred embodiment shown in FIG. 6, all of the ultrasound system was carried by the detachable cart 695. In another preferred embodiment, part of the ultrasound system (i.e., a first medical diagnostic ultrasound imaging system assembly) is integrated in a base, and another part of the ultrasound system (i.e., a second medical diagnostic ultrasound imaging system assembly) is carried by a detachable cart. For example, in FIG. 7, the display device 730 and the user interface 740 of the ultrasound system are integrated with the base 700. The base 700 comprises a coupling section 705 that is used to electrically and physically couple the base 700 with a medical diagnostic ultrasound imaging system cart (not shown) that carries a transducer probe, a beamformer, and a processor. When a mating portion of the cart is coupled with the coupling section 705, the processor carried by the cart is in electrical communication with the display device 730 and the user interface 740. Distributing the components of the ultrasound imaging system between the base 700 and the cart makes the cart more portable. Also, separating the display device 730 and the user interface 740 from the cart can prevent the mechanical instability problem discussed above. Further, this distribution allows the base 700 to act as a "docking station" for the cart, allowing a songrapher to use the larger display device 730 and/or user interface 740 on the base 700 rather than using the display device and/or user interface carried by the cart.

Figure 8:
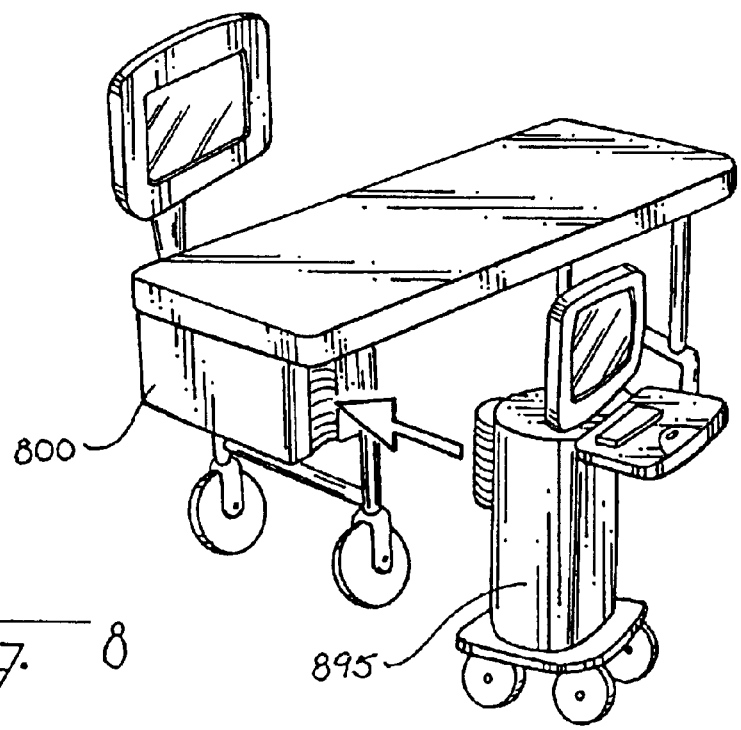
FIG. 8 is an illustration of a medical diagnostic ultrasound imaging system with a patient support surface of another preferred embodiment.

In another embodiment (shown in FIG. 8), the part of the ultrasound system integrated in the base 800 (i.e., the first medical diagnostic ultrasound imaging system assembly) comprises a first processor operative to perform a first set of ultrasound imaging features, and the part of the ultrasound system carried by the detachable cart 895 (i.e., the second medical diagnostic ultrasound imaging system assembly) comprises a second processor operative to perform a second set of ultrasound imaging features. For example, the base 800 can contain the primary ultrasound system and a resident display device that stays with the base 800, and the portable ultrasound system carried by the cart 895 can offer specialized features not available in the primary ultrasound system. Once the cart 895 couples with the base 800, the sonographer has access to the features on both the primary ultrasound system and the portable ultrasound system.

It is intended that the foregoing detailed description be understood as an illustration of selected forms that the invention can take and not as a definition of the invention. It is only the following claims, including all equivalents, that are intended to define the scope of this invention.

What is claimed is:

1. A medical diagnostic ultrasound imaging system with a patient support surface comprising:
    a base;
    a patient support surface coupled with the base; and
    a medical diagnostic ultrasound imaging system cart detachably coupled with the base and carrying:
        a transducer probe;
        a beamformer coupled with the transducer probe;
        a processor coupled with the beamformer;
        a display device coupled with the processor; and
        a user interface coupled with the processor;
    wherein the base and the medical diagnostic ultrasound imaging system cart each comprises at least one respective wheel, and wherein, when the medical diagnostic ultrasound imaging system cart is detachably coupled with the base, the base and the medical diagnostic ultrasound imaging system cart can be wheeled together as a single unit.

2. The invention of claim 1, wherein the base and the medical diagnostic ultrasound imaging system cart comprise means for detachably coupling the base and the medical diagnostic ultrasound imaging system cart.

3. The invention of claim 1, wherein the base comprises a clamping mechanism configured to clamp onto a surface of the medical diagnostic ultrasound imaging system cart.

4. The invention of claim 1, wherein the medical diagnostic ultrasound imaging system cart comprises a clamping mechanism configured to clamp onto a surface of the base.

5. The invention of claim 1, wherein at least one of the display device and user interface is movable with respect to the patient support surface.

6. The invention of claim 5, wherein movement of said at least one of the display device and user interface is limited when the medical diagnostic ultrasound imaging system cart is detached from the base.

7. A medical diagnostic ultrasound imaging system with a patient support surface comprising:
    a base;
    a patient support surface coupled with the base;
    first medical diagnostic ultrasound imaging system assembly integrated with the base, the first medical diagnostic ultrasound imaging system assembly comprising one or more of the following: a transducer probe, a beamformer, a processor, a display device, and a user interface; and
    a medical diagnostic ultrasound imaging system cart detachably and electrically coupled with the base and carrying a second medical diagnostic ultrasound imaging system assembly, the second medical diagnostic ultrasound imaging system assembly comprising one or more of the following: a transducer probe, a beamformer, a processor, a display device, and a user interface.

8. The invention of claim 7, wherein the first medical diagnostic ultrasound imaging system assembly comprises a display device and a user interface, and wherein the second medical diagnostic ultrasound imaging system assembly comprises a transducer probe, a beamformer, and a processor.

9. The invention of claim 7, wherein the first medical diagnostic ultrasound imaging system assembly comprises a first processor operative to perform a first set of ultrasound imaging features, and wherein the second medical diagnostic ultrasound imaging system assembly comprises a second processor operative to perform a second set of ultrasound imaging features.

10. The invention of claim 7, wherein at least one of the display device and user interface is movable with respect to the patient support surface.

11. A medical diagnostic ultrasound imaging system with a patient support surface comprising:

a base;

a patient support surface coupled with the base; and a medical diagnostic ultrasound imaging system cart detachably coupled with the base and carrying:
a transducer probe;
a beamformer coupled with the transducer probe;
a processor coupled with the beamformer;
a display device coupled with the processor; and
a user interface coupled with the processor;

wherein the base and the medical diagnostic ultrasound imaging system cart each comprises at least one respective wheel, and wherein, when the medical diagnostic ultrasound imaging system cart is detachably coupled with the base, movement of said at least one wheel of the base results in movement of said at least one wheel of the medical diagnostic ultrasound imaging system cart.

12. The invention of claim 11, wherein the base and the medical diagnostic ultrasound imaging system cart comprise means for detachably coupling the base and the medical diagnostic ultrasound imaging system cart.

13. The invention of claim 11, wherein the base comprises a clamping mechanism configured to clamp onto a surface of the medical diagnostic ultrasound imaging system cart.

14. The invention of claim 11, wherein the medical diagnostic ultrasound imaging system cart comprises a clamping mechanism configured to clamp onto a surface of the base.

15. The invention of claim 11, wherein at least one of the display device and user interface is movable with respect to the patient support surface.

16. The invention of claim 15, wherein movement of said at least one of the display device and user interface is limited when the medical diagnostic ultrasound imaging system cart is detached from the base.

17. A medical diagnostic ultrasound imaging system with a patient support surface comprising:

a base;

a patient support surface coupled with the base; and a medical diagnostic ultrasound imaging system cart detachably coupled with the base and carrying:
a transducer probe;
a beamformer coupled with the transducer probe;
a processor coupled with the beamformer;
a display device coupled with the processor; and
a user interface coupled with the processor;

wherein at least one of the display device and user interface is movable with respect to the patient support surface, and wherein movement of said at least one of the display device and user interface is limited when the medical diagnostic ultrasound imaging system cart is detached from the base.

18. The invention of claim 17, wherein the base and the medical diagnostic ultrasound imaging system cart comprise means for detachably coupling the base and the medical diagnostic ultrasound imaging system cart.

19. The invention of claim 17, wherein the base comprises a clamping mechanism configured to clamp onto a surface of the medical diagnostic ultrasound imaging system cart.

20. The invention of claim 17, wherein the medical diagnostic ultrasound imaging system cart comprises a clamping mechanism configured to clamp onto a surface of the base.

21. The invention of claim 17, wherein at least one of the base and the medical diagnostic ultrasound imaging system cart comprises wheels.

22. The invention of claim 17, wherein one of the medical diagnostic ultrasound imaging system cart and the base comprises a key and wherein the other comprises a receiving member, and wherein movement of said at least one of the display device and user interface is limited when the key is not engaged in the receiving member.

* * * * *